US012109399B2

(12) United States Patent
Thompson et al.

(10) Patent No.: US 12,109,399 B2
(45) Date of Patent: Oct. 8, 2024

(54) PLUNGER ROD AND ASSEMBLY HAVING MODIFIED THREAD GEOMETRY

(71) Applicant: West Pharmaceutical Services, Inc., Exton, PA (US)

(72) Inventors: James Thompson, Reading, PA (US); Lauren Shafer Greenberg, Barto, PA (US); Matthew Dylan Sweeney, West Chester, PA (US)

(73) Assignee: West Pharmaceutical Services, Inc., Exton, PA (US)

( * ) Notice: Subject to any disclaimer, the term of this patent is extended or adjusted under 35 U.S.C. 154(b) by 856 days.

(21) Appl. No.: 16/973,830

(22) PCT Filed: Jun. 21, 2019

(86) PCT No.: PCT/US2019/038514
§ 371 (c)(1),
(2) Date: Dec. 10, 2020

(87) PCT Pub. No.: WO2019/246543
PCT Pub. Date: Dec. 26, 2019

(65) Prior Publication Data
US 2021/0252228 A1 Aug. 19, 2021

Related U.S. Application Data

(60) Provisional application No. 62/687,992, filed on Jun. 21, 2018.

(51) Int. Cl.
*A61M 5/315* (2006.01)
*A61L 2/18* (2006.01)

(52) U.S. Cl.
CPC ........... *A61M 5/31515* (2013.01); *A61L 2/18* (2013.01); *A61L 2202/23* (2013.01); *A61M 2005/31516* (2013.01); *A61M 2205/02* (2013.01)

(58) Field of Classification Search
CPC .... A61M 5/31515; A61M 2005/31516; A61M 5/31511
See application file for complete search history.

(56) References Cited

U.S. PATENT DOCUMENTS 4,934,379 A * 6/1990 Marzolf ........... A61B 5/150244
604/231
8,007,475 B2 8/2011 Kosinski
(Continued)

FOREIGN PATENT DOCUMENTS

| CN | 106999668 | 8/2017 |
| JP | 2001029469 | 2/2001 |

(Continued)

OTHER PUBLICATIONS

Int'l Search Report and Written Opinion issued Sep. 18, 2019 in Int'l Application No. PCT/US2019/038514.
(Continued)

*Primary Examiner* — Tiffany Legette
*Assistant Examiner* — Macy C Frank
(74) *Attorney, Agent, or Firm* — Blank Rome LLP

(57) ABSTRACT

A fluid-dispensing syringe includes a barrel and a plunger assembly disposed within the barrel. The assembly includes a piston with an outer piston surface, an inner piston cavity with an inner piston surface and at least one female thread, and proximal and distal piston ends. The plunger rod includes a rod body having proximal and distal rod ends, with a threaded extension extending distally from the distal rod end. The threaded extension extends distally along a distal length and threadedly engages the at least one female thread along a portion of the distal length. The threaded extension has a ventilation feature configured to create a ventilation space between the threaded extension and the inner piston surface. The proximal piston end and the distal rod end are in spaced relation to form a primary fluid (Continued)

passageway portion from outside of the plunger assembly into the piston cavity.

20 Claims, 14 Drawing Sheets

(56) References Cited

U.S. PATENT DOCUMENTS

| | | | |
|---|---|---|---|
| 2005/0010175 A1* | 1/2005 | Beedon | A61M 5/31511 604/218 |
| 2013/0030382 A1* | 1/2013 | Sudo | A61M 5/31515 604/224 |
| 2015/0135453 A1* | 5/2015 | Chen | A47L 13/44 15/120.2 |
| 2016/0038684 A1 | 2/2016 | Lum et al. | |
| 2016/0082194 A1* | 3/2016 | Furukawa | A61M 5/31513 604/222 |

FOREIGN PATENT DOCUMENTS

| | | | | |
|---|---|---|---|---|
| JP | 2001061964 | | 3/2001 | |
| JP | 2002272843 | A | 9/2002 | |
| JP | 2007111547 | | 5/2007 | |
| JP | 2011031087 | | 2/2011 | |
| JP | 2011055851 | A | 3/2011 | |
| JP | 2011182944 | | 9/2011 | |
| JP | 2011182944 | A * | 9/2011 | A61M 5/31515 |

OTHER PUBLICATIONS

Int'l Preliminary Report on Patentability issued Dec. 22, 2020 in In'tl Application No. PCT/US2019/038514.

* cited by examiner

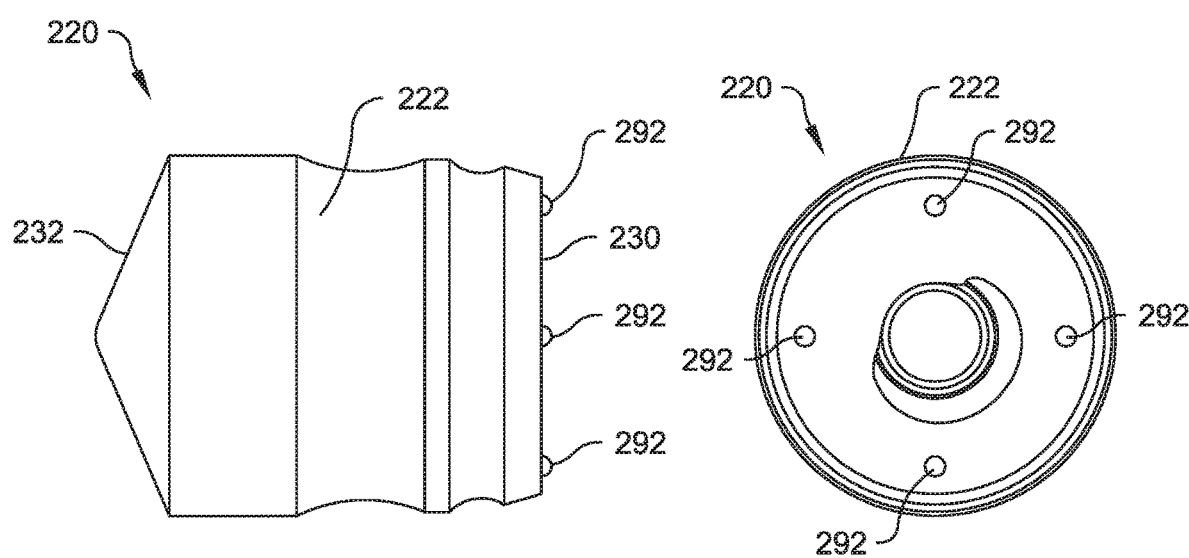
*Fig. 13*  *Fig. 14*

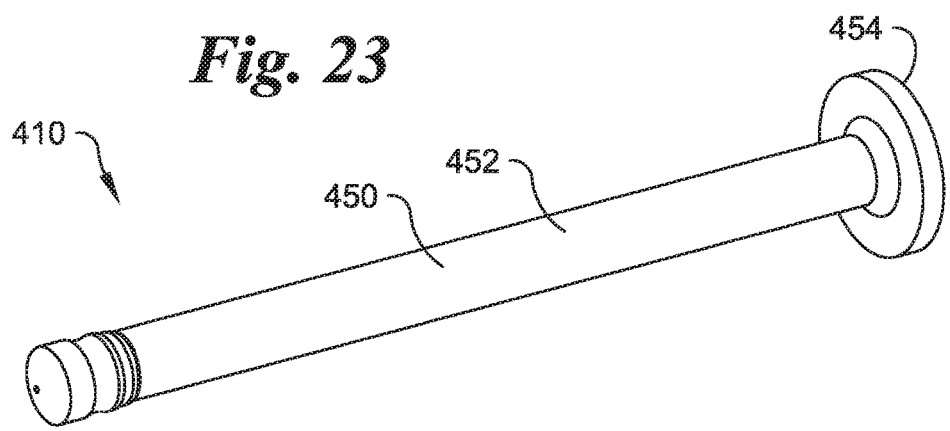
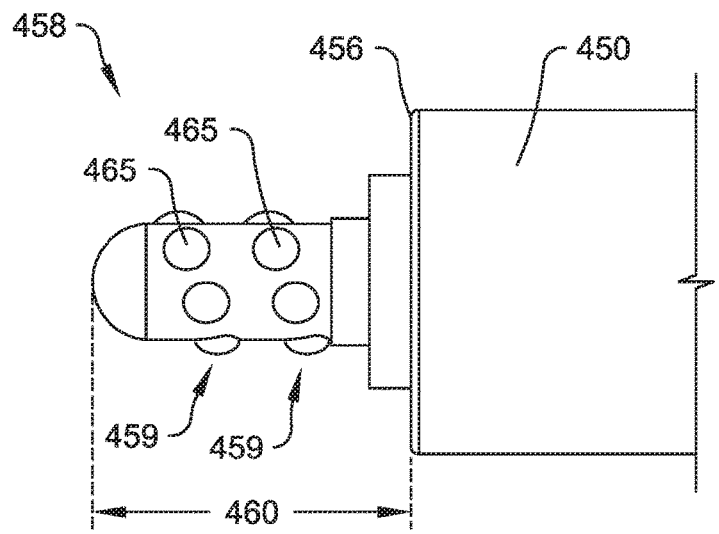
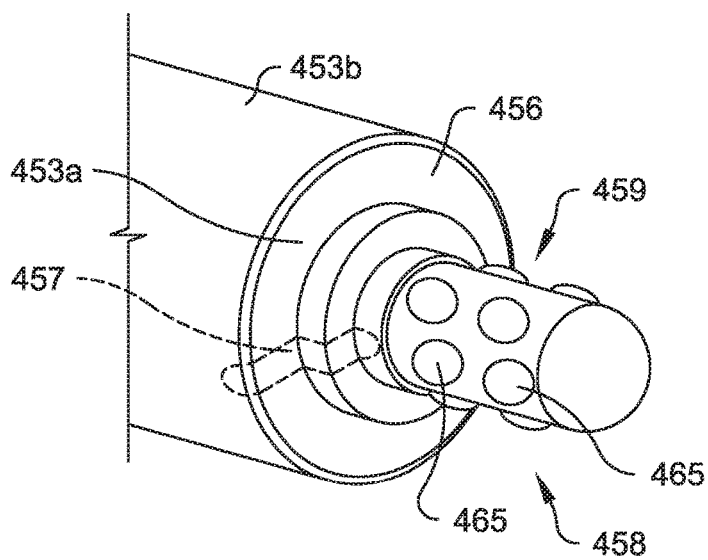

PLUNGER ROD AND ASSEMBLY HAVING MODIFIED THREAD GEOMETRY

CROSS-REFERENCE TO RELATED APPLICATIONS

This application is a Section 371 of International Application No. PCT/US19/38514, filed Jun. 21, 2019, which was published in the English language on Dec. 26, 2019 as International Publication No. WO 2019/246543 A1, which claims priority to U.S. Provisional Application No. 62/687,992, filed Jun. 21, 2018, each of which are hereby incorporated herein by reference in their entireties.

BACKGROUND

This application relates to a syringe having a barrel with plunger assembly inserted therein, wherein the plunger assembly includes a piston and a plunger rod inserted therein. More particularly, this application relates to modifications of the plunger rod that may be used with standard or specialized pistons. This application also relates to modifications of a standard piston. Certain devices disclosed herein may be advantageously used for ocular injections or other injections in which surface sterilization of an internal cavity of a piston may be needed following filling or finishing of a syringe. Standard plunger rods may be limited in that surfaces within the piston cavity may not be subject to decontamination, or may not be conveniently decontaminated, when the standard plunger rod is attached to the piston.

SUMMARY OF THE DISCLOSURE

Briefly stated, a plunger assembly for a fluid-dispensing syringe comprises a piston including an outer piston surface, an inner piston cavity having an inner piston surface and a female thread, a proximal piston end, and a distal piston end. A plunger rod includes a rod body having a proximal rod end and a distal rod end, with a threaded extension extending distally from the distal rod end. The threaded extension is advanced distally along a distal length and threadedly engages the female thread of the piston cavity along at least a portion of the distal length. The threaded extension has a ventilation feature configured with respect to the piston cavity to create a ventilation space between the threaded extension and the inner piston surface. The proximal piston end and the distal rod end are in spaced relation to form a primary fluid passageway portion from outside of the plunger assembly into the ventilation space within the piston cavity.

In certain embodiments, the piston cavity has a proximal cavity end and a distal cavity end and includes a first longitudinal portion with at least one female thread. The first longitudinal portion is spaced apart from the distal cavity end. The threaded extension includes at least one male thread. The male thread has a proximal male thread end and a distal male thread end and is configured so that when the plunger rod is fully advanced distally, the distal rod end is in contact with the proximal piston end, and the proximal male thread end is located distally of the at least one female thread. The ventilation feature comprises a space between the threaded extension and the inner piston surface.

In certain embodiments, the piston cavity has a proximal cavity end and a distal cavity end and includes a first longitudinal portion with at least one female thread. The first longitudinal portion is spaced apart from the distal cavity end. The threaded extension includes at least one male thread extending from a thread shank and having a proximal male thread end and a distal male thread end. The thread shank has a proximal thread shank end and a distal thread shank end, and the proximal male thread end is spaced apart from the proximal thread shank end. The ventilation feature comprises a space between the threaded extension and the inner piston surface. In certain embodiments, the rod body has an outer surface comprising an outer distal end surface and an outer side surface, and the rod body has an auxiliary passage extending from the outer surface and fluidly connecting to the ventilation feature.

In certain embodiments, the piston cavity has a proximal cavity end and a distal cavity end and includes a first longitudinal portion with a plurality of female threads having a female-thread major diameter and a female-thread minor diameter. The threaded extension includes a plurality of male threads extending from a male thread shank and having a constant male thread major diameter. The male thread shank has a proximal male thread shank end, a distal male thread shank end, and a non-constant male thread shank diameter. The ventilation feature comprises a space between the male thread shank and the female-thread minor diameter. In certain embodiments, the ventilation feature comprises a plurality of spaces between the male thread shank and the female-thread minor diameter. In certain embodiments, the rod body has an outer surface comprising an outer distal end surface and an outer side surface, and the rod body has an auxiliary passage extending from the outer surface and fluidly connecting to the ventilation feature. In certain embodiments, the piston cavity has a proximal cavity end and a distal cavity end and includes a first longitudinal portion with a plurality of female threads having a female-thread major diameter and a female-thread minor diameter. The threaded extension includes a plurality of male threads extending from a male thread shank having a male thread shank axis. The male threads have a truncated portion, and the ventilation feature comprises a space between the truncated portion and the female threads. In certain embodiments, the truncated portion includes at least one planar cut portion of the male threads, and the ventilation feature comprises a space between the at least one planar cut portion and the female threads. In certain embodiments, the rod body has an outer surface comprising an outer distal end surface and an outer side surface; and the rod body has an auxiliary passage extending from the outer surface to the truncated portion to connect to the ventilation feature. In certain embodiments, the rod body has an outer surface comprising an outer distal end surface and an outer side surface, and the proximal rod end has an auxiliary passage extending from the outer surface to the truncated portion. In certain embodiments, the auxiliary passage extends from the outer side surface to the truncated portion.

In certain embodiments, the threaded extension comprises a male thread shank and a plurality of protruding bodies extending therefrom. The plurality of protruding bodies have a respective plurality of radially outward portions, and the plurality of radially outward portions are arranged to form a discontinuous male thread. The ventilation feature comprises a plurality of spaces between the plurality of protruding bodies. In certain embodiments, the plurality of protruding bodies comprises at least one of a hemispherical body and a rod-shaped body with a hemispherical radially outward portion. In certain embodiments, the male thread shank has a non-constant male thread shank diameter. In certain embodiments, the rod body has an outer surface comprising an outer distal end surface and an outer side surface, and the rod body has an auxiliary passage extending from the outer surface and fluidly connecting to the ventilation feature.

In another aspect, a fluid-dispensing syringe comprises a syringe barrel having a proximal end and a distal end. The proximal end has a proximal barrel opening. The fluid-dispensing syringe includes a plunger assembly configured as disclosed herein, with the piston of the plunger assembly being disposed within the syringe barrel.

In another aspect, a method of preparing a sterile plunger assembly comprises: engaging a piston with a plunger rod to form a plunger assembly configured as disclosed herein; and introducing a sterilizing fluid into the space outside the plunger assembly so that the sterilizing fluid passes into the piston cavity for sterilization thereof.

In another aspect, a method of preparing a sterile fluid-dispensing syringe comprises: engaging a piston with a plunger rod to form a plunger assembly configured as disclosed herein; inserting the plunger assembly into a barrel having a proximal end and a distal end, the proximal end having a proximal barrel opening; and introducing a sterilizing fluid into the space outside the plunger assembly so that the sterilizing fluid passes into the piston cavity for sterilization thereof.

In another aspect, a syringe plunger rod comprises a rod body having a proximal rod end and a distal rod end. The distal rod end has a distal rod end circumference. A threaded extension extends distally from the distal rod end. The threaded extension includes at least one male thread extending from a thread shank. The thread shank has a proximal thread shank end and a distal thread shank end. The proximal thread shank end has a diameter less than the diameter of the distal rod end circumference. An annular distal rod surface extends between the distal rod end circumference and the proximal thread shank end. The annular distal rod surface includes at least one auxiliary passage. The auxiliary passage defines a channel positioned between the distal rod end circumference and the proximal thread shank end. In certain embodiments, the channel extends at least radially outwardly to the distal rod end circumference. In certain embodiments, the channel extends at least radially inwardly to the proximal thread shank end. In certain embodiments, the channel extends at least radially inwardly terminating before the proximal thread shank end. In certain embodiments, the channel does not extend distally beyond the at least one male thread. In certain embodiments, the syringe plunger rod is comprised of a polymeric material.

In another aspect, a syringe plunger rod comprises a rod body having a proximal rod end and a distal rod end. The distal rod end has a distal rod end circumference. A threaded extension extends distally from the distal rod end. The threaded extension includes at least one male thread extending from a thread shank. The thread shank has a proximal thread shank end and a distal thread shank end. The proximal thread shank end has a diameter less than the diameter of the distal rod end circumference. An annular distal rod surface extends between the distal rod end circumference and the proximal thread shank end. The annular distal rod surface includes at a plurality of protrusions extending distally. In certain embodiments, the plurality of protrusions does not extend distally beyond the at least one male thread. In certain embodiments, the syringe plunger rod is comprised of a polymeric material.

Features and elements disclosed herein may be employed in any combination within a particular device or method.

BRIEF DESCRIPTION OF THE DRAWINGS

The foregoing summary, as well as the following detailed description, will be better understood when read in conjunction with the appended drawings. For the purpose of illustrating embodiments of the invention, there are shown in the drawings embodiments which are presently preferred. It should be understood, however, that the invention is not limited to the precise arrangements and instrumentalities shown. In the drawings:

FIG. 13 is a right side elevational view of the piston of FIG. 9;

FIG. 14 is a rear elevational view of the piston of FIG. 9;

FIG. 23 is a front right perspective view of a fourth embodiment of a plunger assembly;

FIG. 24 is a magnified partial right side elevational view of the plunger of FIG. 23;

FIG. 25 is a magnified partial sectional view of the plunger of FIG. 23;

DETAILED DESCRIPTION

Figure 1:
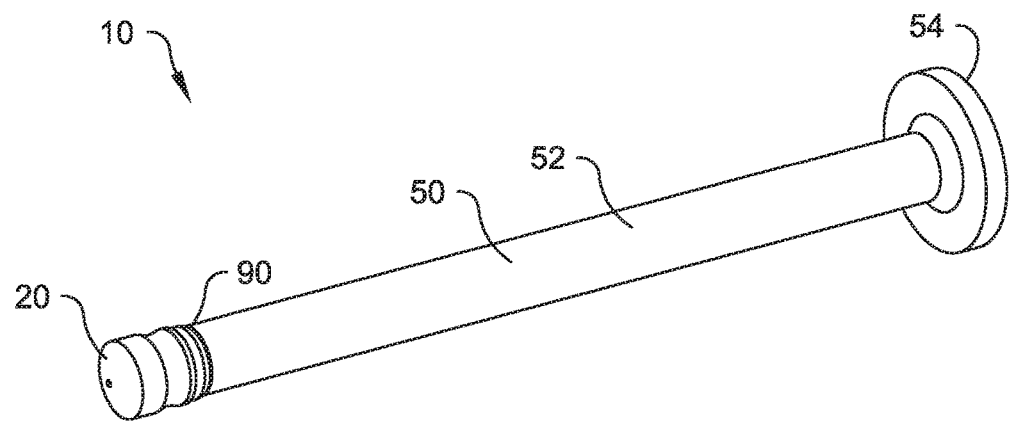
FIG. 1 is a front right perspective view of a first embodiment of a plunger assembly.
Figure 2:
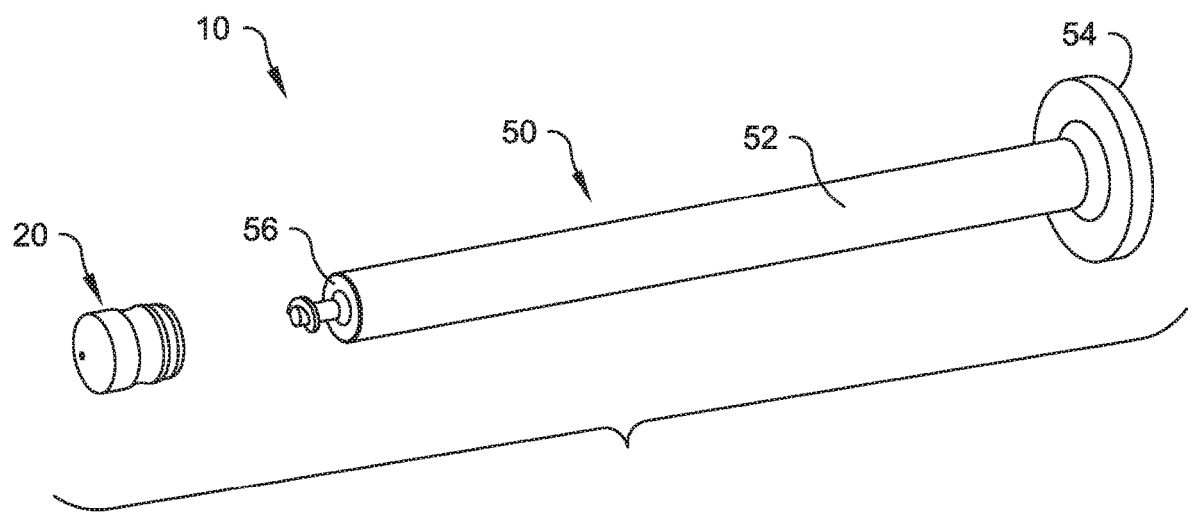
FIG. 2 is a front right perspective exploded view of the plunger and the piston of FIG. 1.
Figure 3:
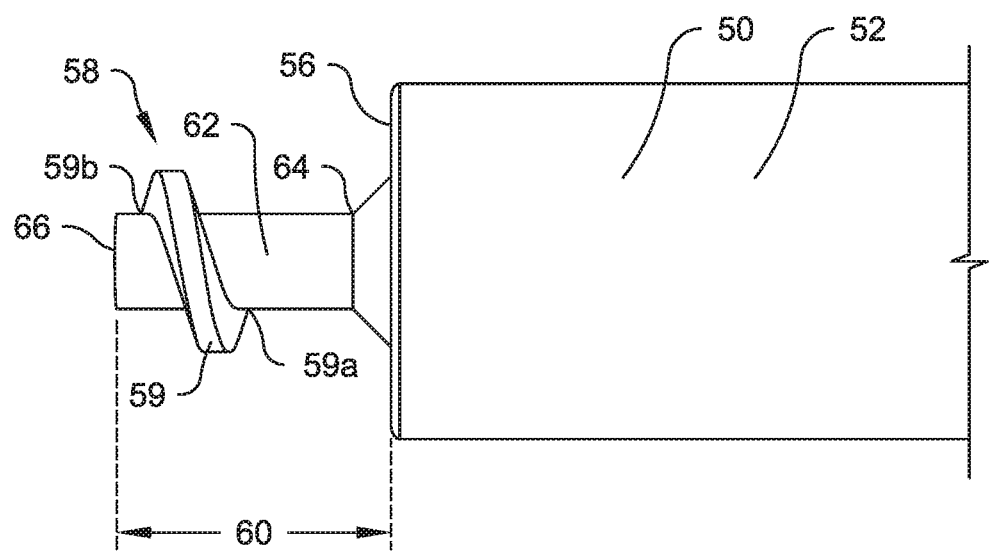
FIG. 3 is a magnified partial right side elevational view of the plunger of FIG. 1.
Figure 4:
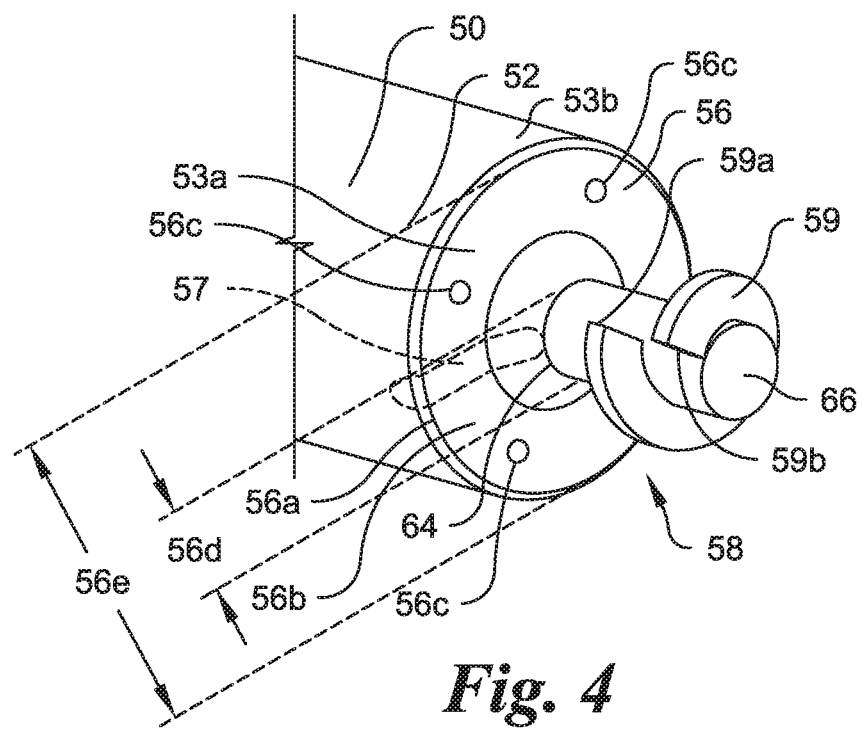
FIG. 4 is a magnified partial front left perspective view of the plunger of FIG. 1.
Figure 5:
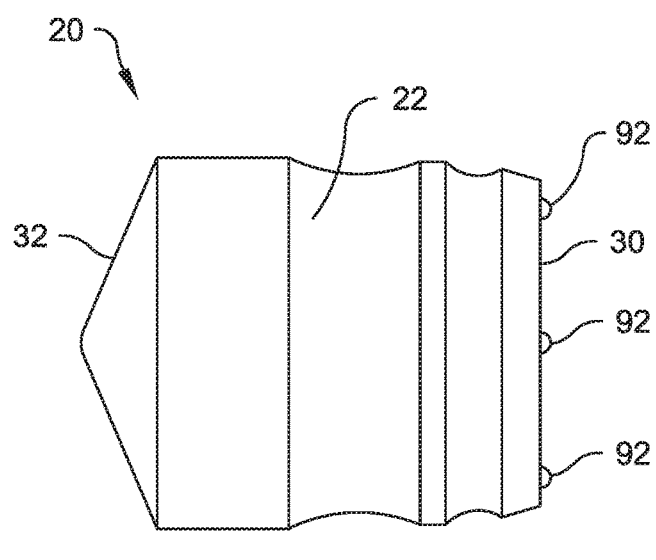
FIG. 5 is a right side elevational view of the piston of FIG. 1.
Figure 6:
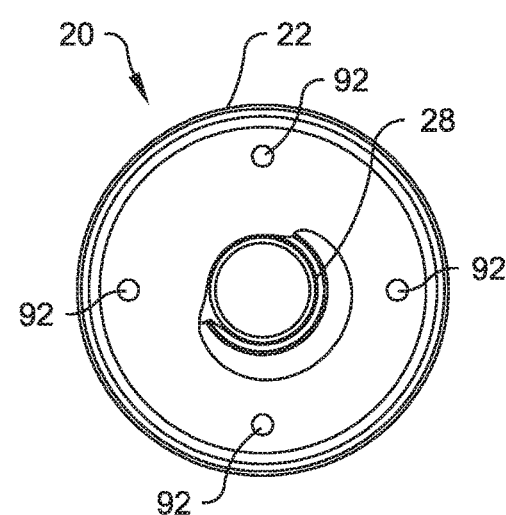
FIG. 6 is a rear elevational view of the piston of FIG. 1.
Figure 7:
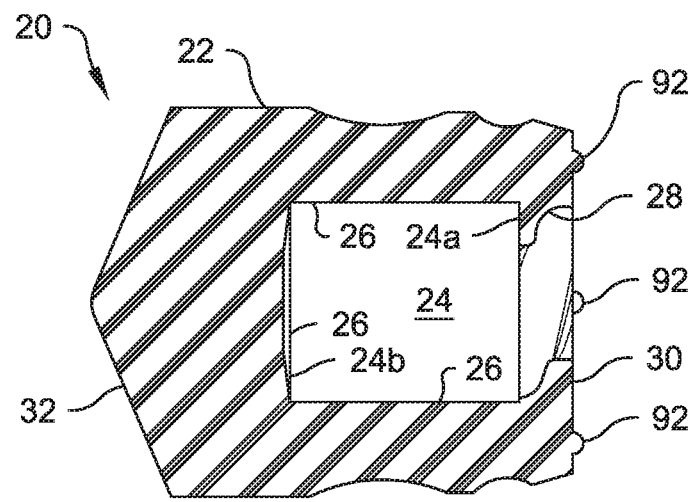
FIG. 7 is a magnified right side partial sectional view of the piston of FIG. 1.
Figure 8:
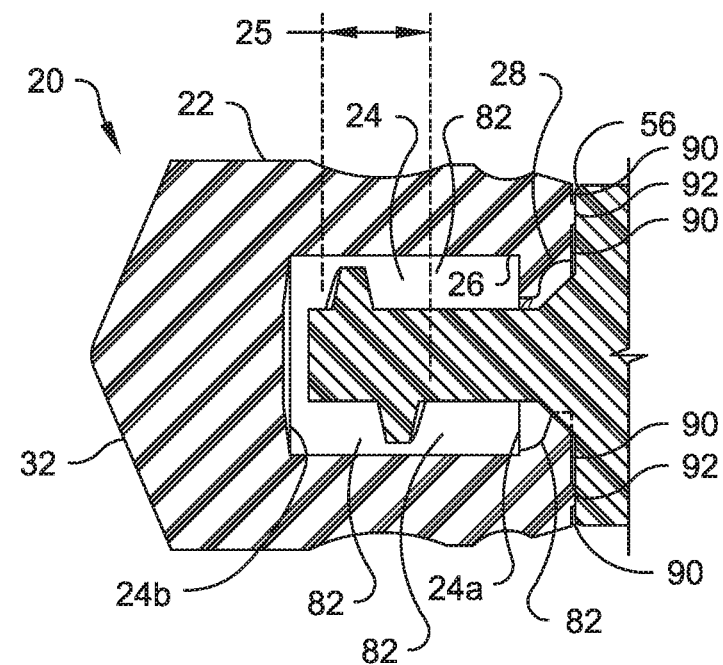
FIG. 8 is a magnified right side partial sectional view of the plunger assembly of FIG. 1.
Figure 9:
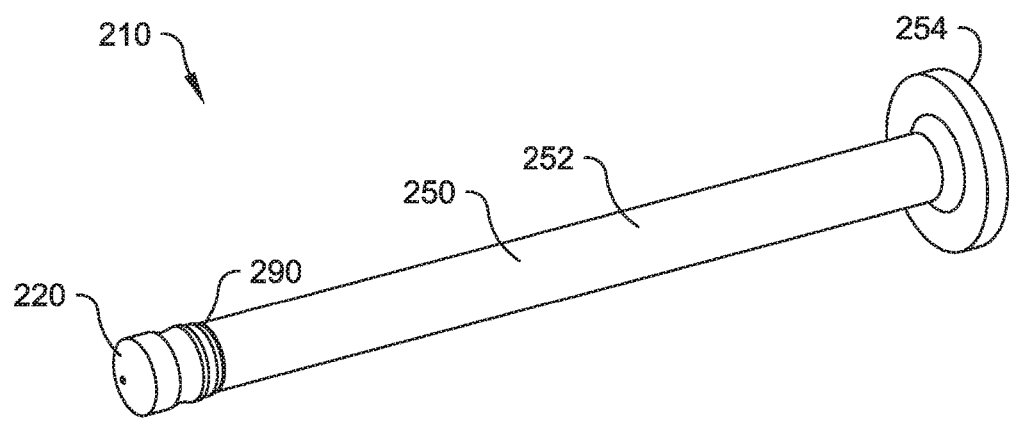
FIG. 9 is a front right perspective view of a second embodiment of a plunger assembly.
Figure 10:
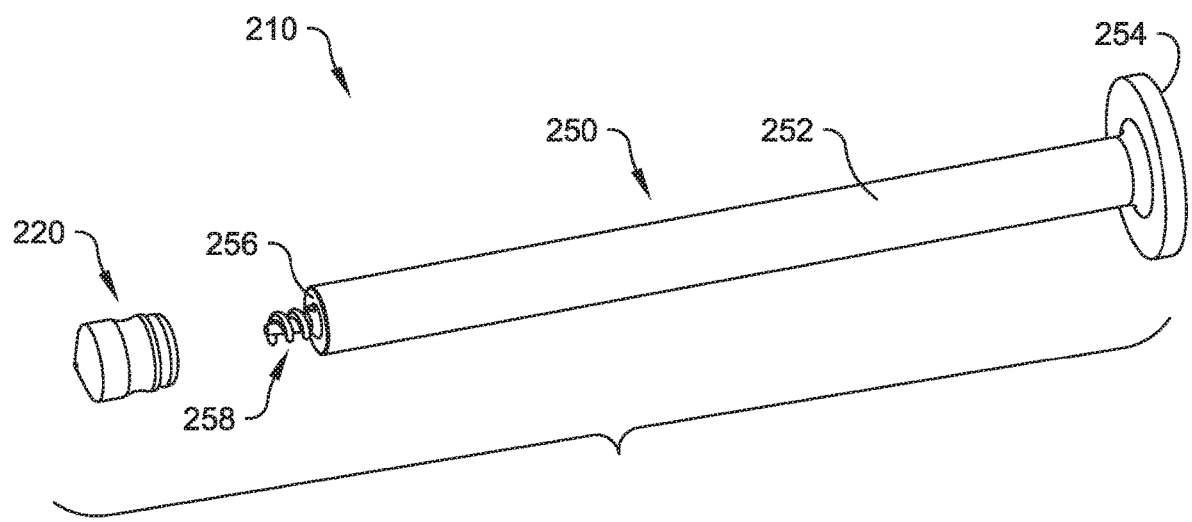
FIG. 10 is a front right perspective exploded view of the plunger and the piston of FIG. 9.
Figure 11:
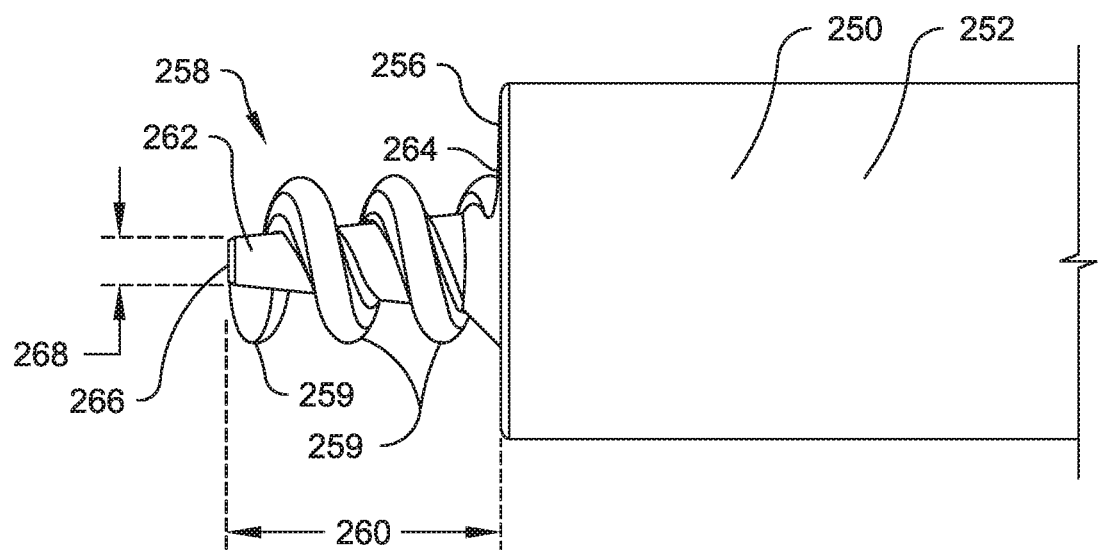
FIG. 11 is a magnified partial right side elevational view of the plunger of FIG. 9.
Figure 12:
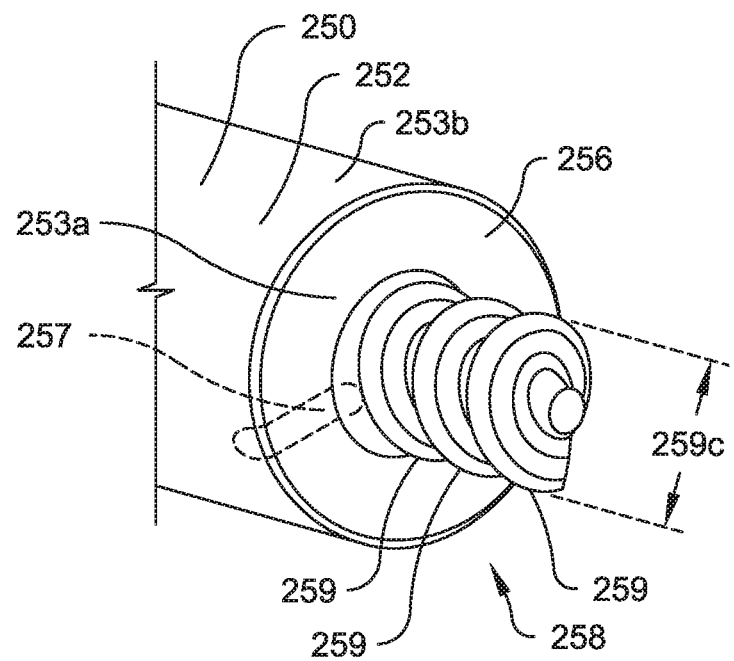
FIG. 12 is a magnified partial front left perspective view of the plunger of FIG. 9.
Figure 15:
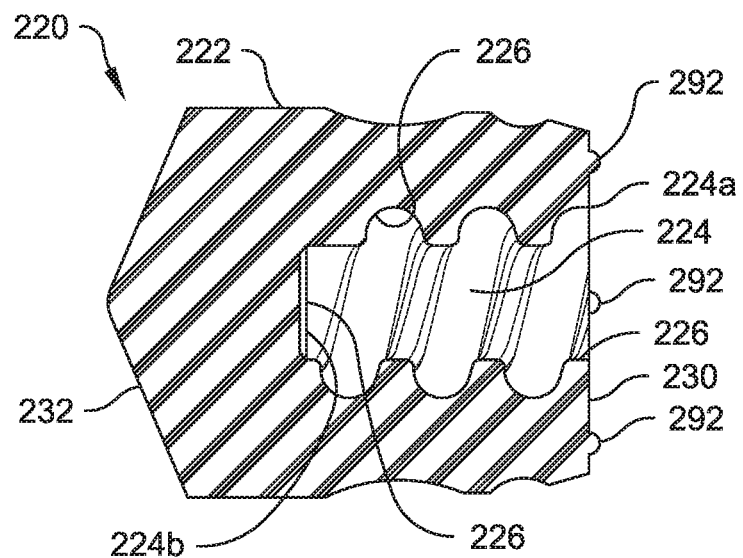
FIG. 15 is a magnified right side partial sectional view of the piston of FIG. 9.
Figure 16:
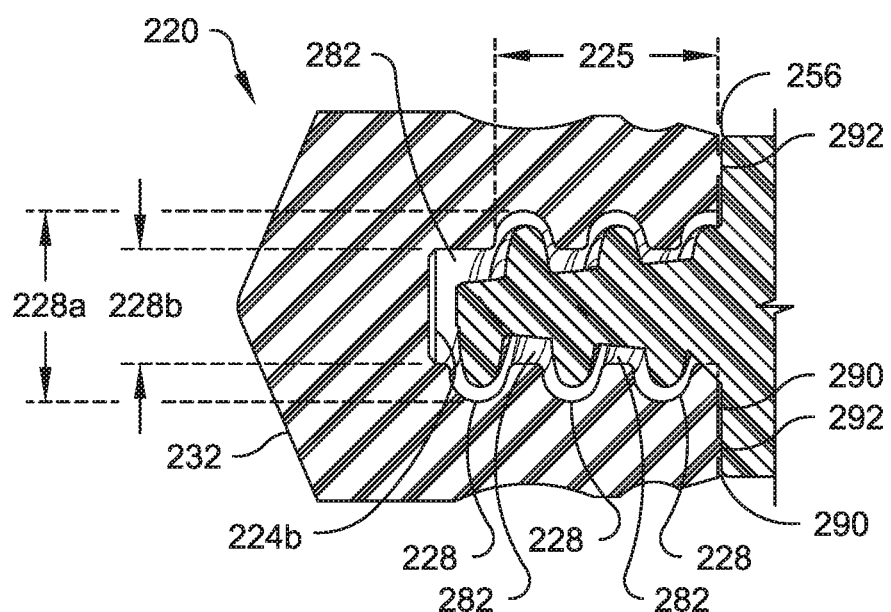
FIG. 16 is a magnified right side partial sectional view of the plunger assembly of FIG. 9.
Figure 17:
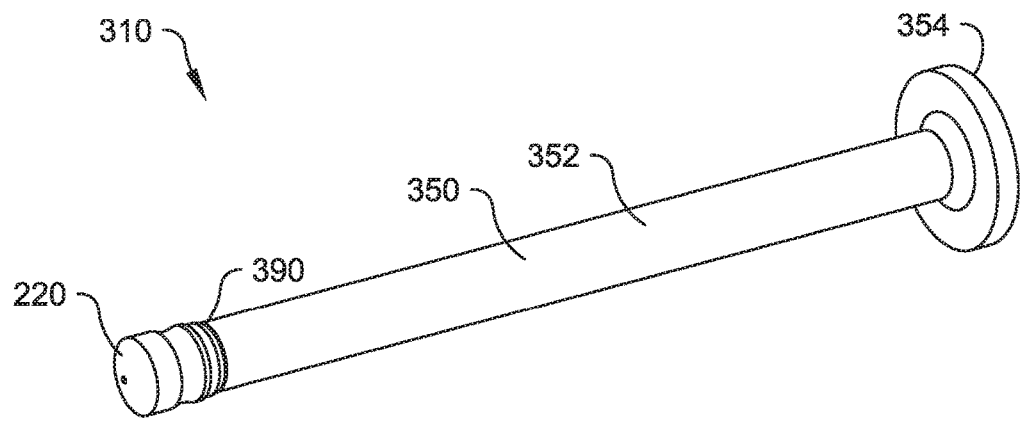
FIG. 17 is a front right perspective view of a third embodiment of a plunger assembly.
Figure 18:
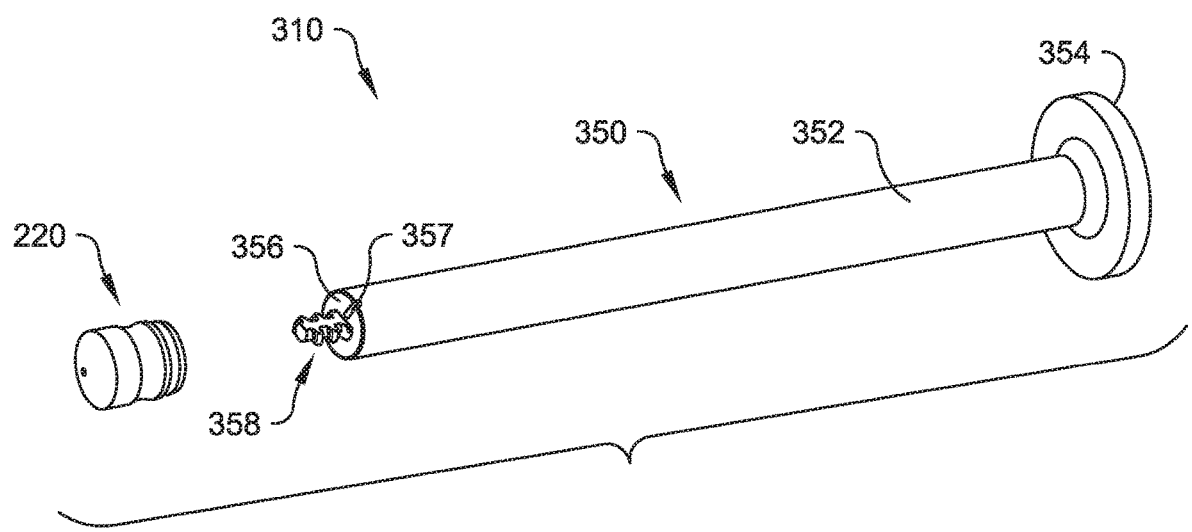
FIG. 18 is a front right perspective exploded view of the plunger and the piston of FIG. 17.
Figure 19:
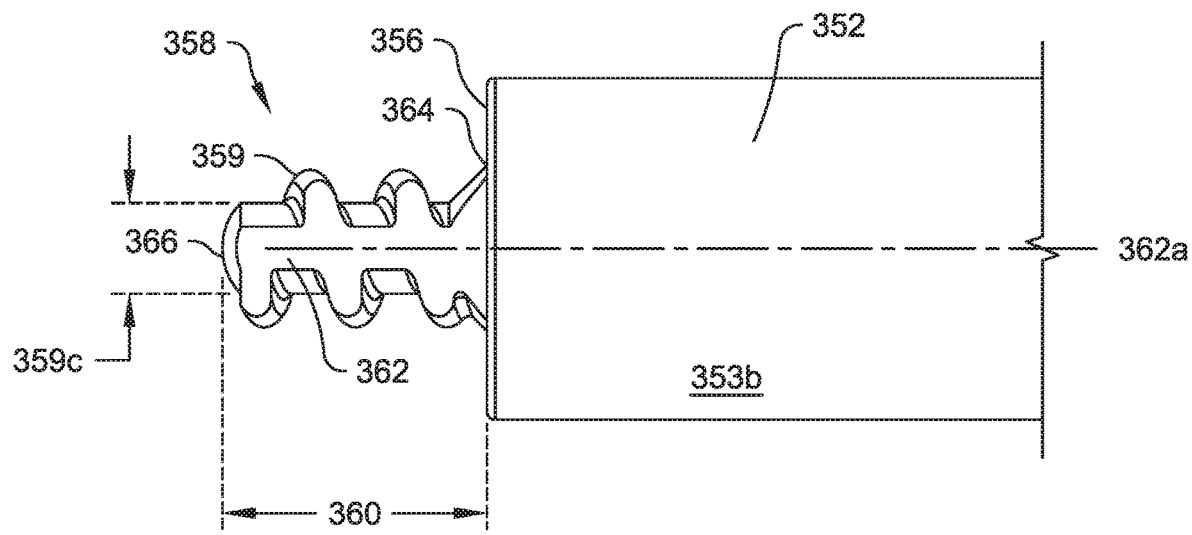
FIG. 19 is a magnified partial right side elevational view of the plunger of FIG. 17.
Figure 20:
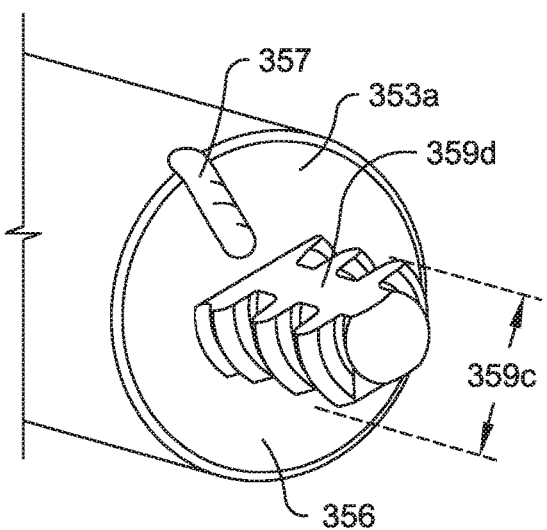
FIG. 20 is a magnified partial front left perspective view of the plunger of FIG. 17.
Figure 21:
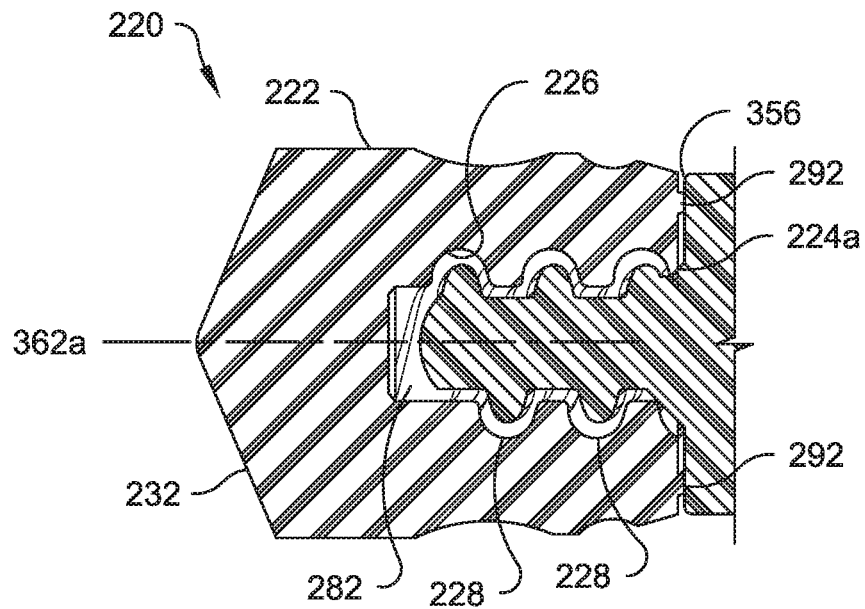
FIG. 21 is a magnified right side partial sectional view of the plunger assembly of FIG. 17, with the flat sides of the threads oriented perpendicular to the plane of the page.
Figure 22:
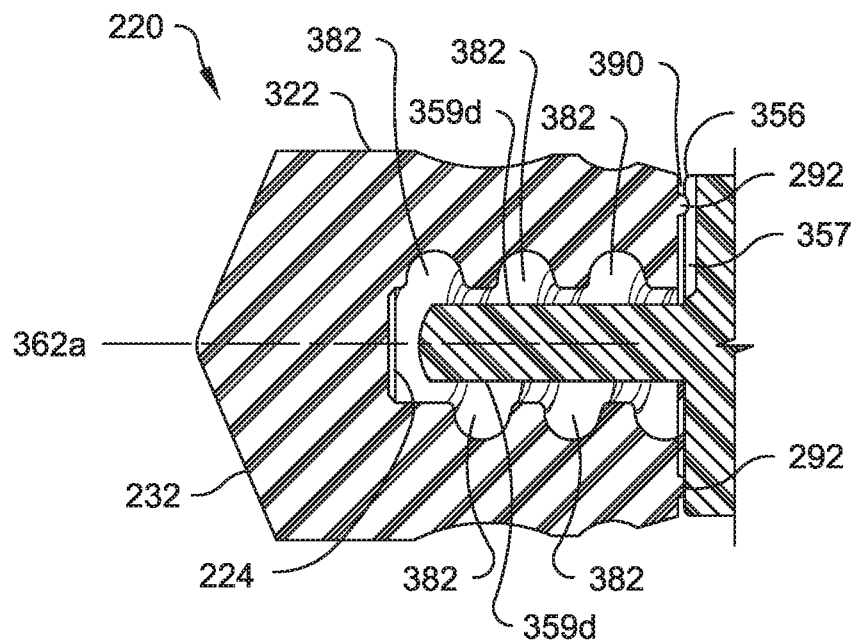
FIG. 22 is a magnified right side partial sectional view of the plunger assembly of FIG. 17, with the flat sides of the threads oriented parallel to the plane of the page.

Referring to FIGS. 1-8, a first embodiment of a plunger assembly 10 for a fluid-dispensing syringe may comprise a piston 20 and a syringe plunger rod/plunger rod 50. The piston 20 may be formed of rubber, a suitable elastomer, or other suitable material, may be generally cylindrical, and may include an outer piston surface 22, an inner piston cavity 24 having an inner piston surface 26 and a female thread 28, a proximal piston end 30 and a distal piston end 32. The plunger rod 50 may be formed from or comprised of a suitable polymeric material, elastomeric material, or another suitable material and may include a rod body 52 having a proximal rod end 54 and a distal rod end 56 and any suitable cross-section, including cylindrical (as shown), polygonal, or cross shaped. The distal rod end 56 may have a distal rod end circumference 56a and an annular distal rod surface 56b extending between the distal rod end circumference 56a and the proximal thread shank end 64. The distal rod end circumference 56a may have a distal rod end circumference diameter 56e. A threaded extension 58 may extend distally from the distal rod end 56. The threaded extension 58 may extend distally along a distal length 60 and may threadedly engage the female thread 28 of the piston cavity 24, which may include at least one female thread 28, along at least a portion of the distal length 60. The threaded extension 58 may engage and may couple to the at least one female thread 28 such that the plunger rod 50 may move the piston 20 proximally as well as distally. The threaded extension 58 may have a ventilation feature configured with respect to the piston cavity 24 to create a ventilation space, which may comprise a space 82 between the threaded extension 58 and the inner piston surface 26. The rod body 52 may have an outer surface comprising an outer distal end surface 53a and an outer side surface 53b (FIG. 4), and the proximal rod end 356 may have an auxiliary passage 57 (shown in dashed lines in FIG. 4) extending from the outer surface to the ventilation feature, which may include the spaces 82. The annular distal rod surface 56b may include at least one auxiliary passage defining a channel 57 positioned between the distal rod end circumference 56a and the proximal thread shank end 64. The annular distal rod surface 56b may include a plurality of protrusions 56c extending distally. The plurality of protrusions 56c may not extend distally beyond the at least one male thread 59. The channel 57 may extend at least radially outwardly to the distal rod end circumference 56a. The channel 57 may extend at least radially inwardly to the proximal thread shank end 64. The channel 57 may extend at least radially inwardly terminating before the proximal thread shank end 64. The channel 57 may not extend distally beyond the at least one male thread 59. The proximal piston end 30 and the distal rod end 56 may be in spaced relation to form a primary fluid passageway portion 90 from outside of the plunger assembly 10 into the piston cavity 24. One or more protrusions 92 may extend proximally from the proximal piston end 30 of the piston 24 to maintain such spacing; alternatively, protrusions may extend from the distal rod end 56 to maintain such spacing. The piston cavity 24 may have a proximal cavity end 24a and a distal cavity end 24b and may include a first longitudinal portion 25, which may be spaced apart from the distal cavity end 24b. The threaded extension 58 may include at least one male thread 59. The male thread 59 may have a proximal male thread end 59a and a distal male thread end 59b and may be configured so that when the plunger rod 50 is fully advanced distally, the distal rod end 56 may be in contact with the protrusions 92 of the proximal piston end 30, and the proximal male thread end 59a may be located distally of the at least one female thread 28 of the piston cavity 24, such that a fluid path may extent from outside of the piston 20 to the piston cavity 24 by way of the primary fluid passageway portion 90 and the female thread 28. The male thread 59 of the threaded extension 58 may extend from a thread shank 62 having a proximal thread shank end 64 and a distal thread shank end 66. The proximal thread shank end 64 has a diameter 56d less than the diameter 56e of the distal rod end circumference 56a. The distal shank end 66 also may have protrusions extending therefrom to maintain spacing between the proximal piston end 30 and the distal rod end 56. The proximal male thread end 59a may be spaced apart from the proximal thread shank end 64. The ventilation feature may include one or more spaces 82, which may provide a volume into which a fluid may flow. The primary fluid passageway portion 90 and the ventilation feature including the one or more spaces 82 may cooperate to provide a fluid path for a fluid (including but not limited to a disinfecting gas) to pass from outside of the plunger assembly 10 into the piston cavity 24 to sterilize the piston cavity 24.

Referring to FIGS. 1-8, a first embodiment of a plunger assembly 10 for a fluid-dispensing syringe may comprise a piston 20 and a syringe plunger rod/plunger rod 50. The piston 20 may be formed of rubber, a suitable elastomer, or other suitable material, may be generally cylindrical, and may include an outer piston surface 22, an inner piston cavity 24 having an inner piston surface 26 and a female thread 28, a proximal piston end 30 and a distal piston end 32. The plunger rod 50 may be formed from or comprised of a suitable polymeric material, elastomeric material, or another suitable material and may include a rod body 52 having a proximal rod end 54 and a distal rod end 56 and any suitable cross-section, including cylindrical (as shown), polygonal, or cross shaped. The distal rod end 56 may have a distal rod end circumference 56a and an annular distal rod surface 56b extending between the distal rod end circumference 56a and the proximal thread shank end 64. The distal rod end circumference 56a may have a distal rod end circumference diameter 56e. A threaded extension 58 may extend distally from the distal rod end 56. The threaded extension 58 may extend distally along a distal length 60 and may threadedly engage the female thread 28 of the piston cavity 24, which may include at least one female thread 28, along at least a portion of the distal length 60. The threaded extension 58 may engage and may couple to the at least one female thread 28 such that the plunger rod 50 may move the piston 20 proximally as well as distally. The threaded extension 58 may have a ventilation feature configured with respect to the piston cavity 24 to create a ventilation space, which may comprise a space 82 between the threaded extension 58 and the inner piston surface 26. The rod body 52 may have an outer surface comprising an outer distal end surface 53a and an outer side surface 53b (FIG. 4), and the distal rod end 56 may have an auxiliary passage 57 (shown in dashed lines in FIG. 4) extending from the outer surface to the ventilation feature, which may include the spaces 82. The annular distal rod surface 56b may include at least one auxiliary passage defining a channel 57 positioned between the distal rod end circumference 56a and the proximal thread shank end 64. The annular distal rod surface 56b may include a plurality of protrusions 56c extending distally. The plurality of protrusions 56c may not extend distally beyond the at least one male thread 59. The channel 57 may extend at least radially outwardly to the distal rod end circumference 56a. The channel 57 may extend at least radially inwardly to the proximal thread shank end 64. The channel 57 may extend at least radially inwardly terminating before the proximal thread shank end 64. The channel 57 may not extend distally beyond the at least one male thread 59. The proximal piston end 30 and the distal rod end 56 may be in spaced relation to form a primary fluid passageway portion 90 from outside of the plunger assembly 10 into the piston cavity 24. One or more protrusions 92 may extend proximally from the proximal piston end 30 of the piston 24 to maintain such spacing; alternatively, protrusions may extend from the distal rod end 56 to maintain such spacing. The piston cavity 24 may have a proximal cavity end 24a and a distal cavity end 24b and may include a first longitudinal portion 25, which may be spaced apart from the distal cavity end 24b. The threaded extension 58 may include at least one male thread 59. The male thread 59 may have a proximal male thread end 59a and a distal male thread end 59b and may be configured so that when the plunger rod 50 is fully advanced distally, the distal rod end 56 may be in contact with the protrusions 92 of the proximal piston end 30, and the proximal male thread end 59a may be located distally of the at least one female thread 28 of the piston cavity 24, such that a fluid path may extent from outside of the piston 20 to the piston cavity 24 by way of the primary fluid passageway portion 90 and the female thread 28. The male thread 59 of the threaded extension 58 may extend from a thread shank 62 having a proximal thread shank end 64 and a distal thread shank end 66. The proximal thread shank end 64 has a diameter 56d less than the diameter 56e of the distal rod end circumference 56a. The distal shank end 66 also may have protrusions extending therefrom to maintain spacing between the proximal piston end 30 and the distal rod end 56. The proximal male thread end 59a may be spaced apart from the proximal thread shank end 64. The ventilation feature may include one or more spaces 82, which may provide a volume into which a fluid may flow. The primary fluid passageway portion 90 and the ventilation feature including the one or more spaces 82 may cooperate to provide a fluid path for a fluid (including but not limited to a disinfecting gas) to pass from outside of the plunger assembly 10 into the piston cavity 24 to sterilize the piston cavity 24.

Referring to FIGS. 9-16, a second embodiment of a plunger assembly 210 for a fluid-dispensing syringe may comprise a piston 220 and a plunger rod 250. The piston 220 may be formed of rubber, a suitable elastomer, or other suitable material and may include an outer piston surface 222, an inner piston cavity 224 having an inner piston surface 226 and a plurality of female threads 228, a proximal piston end 230 and a distal piston end 232. The plunger rod 250 may be formed of a suitable polymeric material, elastomeric material, or another suitable material and may include a rod body 252 having a proximal rod end 254 and a distal rod end 256. A threaded extension 258 may extend distally from the distal rod end 256. The threaded extension 258 may extend distally along at least a portion of a distal length 260 and may threadedly engage the female threads 228 of the piston cavity 224 along at least a portion of the distal length 260. The threaded extension 258 may engage and may couple to the female threads 228 such that the plunger rod 250 may move the piston 220 proximally as well as distally. The threaded extension 258 may have a ventilation feature configured with respect to the piston cavity 224 to create a ventilation space, which may comprise one or a plurality of spaces 282 between the threaded extension 258 and the inner piston surface 226. The proximal piston end 230 and the distal rod end 256 may be in spaced relation to form a primary fluid passageway portion 290 from outside of the plunger assembly 210 into the piston cavity 224. The rod body 252 may have an outer surface comprising an outer distal end surface 253a and an outer side surface 253b (FIG. 12), and the distal rod end 256 may have an auxiliary passage 257 (shown in dashed lines in FIG. 12) extending from the outer surface to the ventilation feature, which may include the spaces 282. The piston cavity 224 may have a proximal cavity end 224a and a distal cavity end 224b and may include a first longitudinal portion 225, which may have a plurality of female threads 228 having a female-thread major diameter 228a and a female-thread minor diameter 228b. The threaded extension 258 may include a plurality of male threads 259 extending from a male thread shank 262. The male threads 259 may have a constant male thread major diameter 259c, which may be selected to be compatible with the female threads 228 of the piston 224. The male thread shank 262 may have a proximal male thread shank end 264 and a distal male thread shank end 266, and a non-constant male thread shank diameter 268, which may be, for example, a tapered male thread shank diameter as shown. The tapering of other variation of the non-constant male thread shank diameter 268 may create spaces 282 between the male thread shank 262 and the female threads 228. The spaces 282 may provide an additional open volume into which fluid may flow as compared to a male thread shank 262 having a constant male thread shank diameter (not shown). The ventilation feature may comprise a plurality of spaces 282 between the male thread shank 262 and the female-thread minor diameter 228b of the piston 220. The ventilation feature may comprise a plurality of spaces 282 between the major thread diameter 259c and the female-thread minor diameter 228b of the piston 220. The primary fluid passageway portion 290 may connect to the spaces 282 and may cooperate to provide a fluid path for a fluid (including but not limited to a disinfecting gas) to pass from outside of the plunger assembly 210 into the piston cavity 224 to sterilize the piston cavity 224.

Referring to FIGS. 17-22, a third embodiment of a plunger assembly 310 for a fluid-dispensing syringe may comprise a piston 220, which may have the same configuration discussed above with respect to the second embodiment, and a plunger rod 350. The piston 220 may be formed of rubber, a suitable elastomer, or other suitable material and may include an outer piston surface 222, an inner piston cavity 224 having a proximal cavity end 224a, a distal cavity end 224b, an inner piston surface 226, and a first longitudinal portion 225 with a plurality of female threads 228, a proximal piston end 230 and a distal piston end 232. The female threads 228 may have a female-thread major diameter 228a and female-thread minor diameter 228b. The plunger rod 350 may be formed of a suitable polymeric material, elastomeric material, or another suitable material and may include a rod body 352 having a proximal rod end 354 and a distal rod end 356. A threaded extension 358 may extend distally from the distal rod end 356. The threaded extension 358 may include a plurality of male threads 359 extending from a male thread shank 362 having a male thread shank axis 363. The male threads 359 may have at least one truncated portion 359d (two are shown), which may be formed by shaping the male threads 359 to be altered in shape, such as by having one or more flattened portions providing shape between the male threads 359 and the inner piston surface 226. The male thread shank 362 may have a proximal thread shank end 364 and a distal thread shank end 366. The threaded extension 358 may extend distally along at least a portion of a distal length 360 and may threadedly engage the female threads 228 of the piston cavity 224 along at least a portion of the distal length 360. The threaded extension 358 may engage and may couple to the female threads 228 such that the plunger rod 350 may move the piston 220 proximally as well as distally. The threaded extension 358 may have a ventilation feature 380 configured with respect to the piston cavity 224 to create a ventilation space, which may comprise one or a plurality of spaces 382 between the threaded extension 358 and the inner piston surface 226 and in particular may comprise one or a plurality of spaces 382 between the truncated portions of the male threads 359, which may take the form of spaces 382 between the planar cut portions 359*d* and the female threads 228 of the piston cavity 224. The spaces 382 may provide an additional open volume into which fluid may flow as compared to a threaded extension lacking planar cut portions 359*d* and other truncated portions. The proximal piston end 230 and the distal rod end 356 may be in spaced relation to form a primary fluid passageway portion 390 from outside of the plunger assembly 310 into the piston cavity 224. The rod body 352 may have an outer surface comprising an outer distal end surface 353*a* and an outer side surface 353*b*, and the distal rod end 356 may have an auxiliary passage 357 extending from the outer surface to the ventilation feature, which may include the spaces 382. The auxiliary passage 357 may extend from the outer distal end surface 353*a* or the outer side surface 353*b* (as shown) of the outer surface 353 of the rod body 352 to one or more of the planar cut portions 359*d*, which may be one type of truncated portion of the male threads 359. The auxiliary passage 357 may provide additional ventilation capacity beyond that provided by the primary fluid passageway portion 390. The ventilation feature may include the spaces 382. The primary fluid passageway portion 390 may connect to the spaces 382 and may cooperate to provide a fluid path for a fluid (including but not limited to a disinfecting fluid) to pass from outside of the plunger assembly 310 into the piston cavity 224 to sterilize the piston cavity 224. An auxiliary passage may be incorporated into any of the plunger rods 50, 250, 350, 450 disclosed herein, with the auxiliary passage in any case being a passage connecting the outside of the plunger assembly with a ventilation feature of the plunger rod 50, 250, 350, 450.

Referring to FIGS. 23-27, a fourth embodiment of a plunger assembly 410 for a fluid-dispensing syringe may comprise a piston 220, which may have the same configuration discussed above with respect to the second embodiment, and a plunger rod 450. The piston 220 may be formed of rubber, a suitable elastomer, or other suitable material and may include an outer piston surface 222, an inner piston cavity 224 having an inner piston surface 226 and a plurality of female threads 228, a proximal piston end 230 and a distal piston end 232. The plunger rod 450 may be formed of a suitable polymeric material, elastomeric material, or another suitable material and may include a rod body 452 having a proximal rod end 454 and a distal rod end 456. A threaded extension 458 may extend distally from the distal rod end 456. The threaded extension 458 may extend distally along a distal length 460 and may threadedly engage the female threads 228 of the piston cavity 224 along at least a portion of the distal length 460. The threaded extension 458 may engage and may couple to the female threads 228 such that the plunger rod 450 may move the piston 220 proximally as well as distally. The threaded extension 458 may have a ventilation feature configured with respect to the piston cavity 224 to create a ventilation space, which may comprise a space 482 between the threaded extension 458 and the inner piston surface 226. The proximal piston end 230 and the distal rod end 456 may be in spaced relation to form a primary fluid passageway portion 490 from outside of the plunger assembly 410 into the piston cavity 224. The rod body 452 may have an outer surface comprising an outer distal end surface 453*a* and an outer side surface 453*b* (FIG. 25), and the distal rod end 456 may have an auxiliary passage 457 (shown in dashed lines in FIG. 25) extending from the outer surface to the ventilation feature, which may include the spaces 482. The threaded extension 458 may comprise a male thread shank 462 and a plurality of protruding bodies 463, 465 extending therefrom, including at least one of a hemispherical body 463 and a rod-shaped body with a hemispherical body attached thereto 465. Each protruding body 463, 465 has a respective radially outward portion 463*a*, 465*a*, which are arranged and configured to form a discontinuous male thread. The heights of the protruding bodies 463, 465 on a particular device need not be identical. The ventilation feature may comprise a plurality of spaces 482 between the plurality of protruding bodies 463, 465. The spaces 482 may provide an additional open volume into which fluid may flow as compared to a male thread shank lacking such protruding bodies 463, 465 and spaces 482. The male thread shank 462 is shown with a constant diameter may have a non-constant male thread shank diameter (not shown in this embodiment, but see element 268, FIGS. 9-16) such as a tapered, undulating, or stepped diameter. The ventilation feature, which may include one or more spaces 482, and the primary fluid passageway portion 490 may cooperate to provide a fluid path for a fluid to pass from outside the plunger assembly 410 into the piston cavity 224 to sterilize the piston cavity 224.

Figure 26:
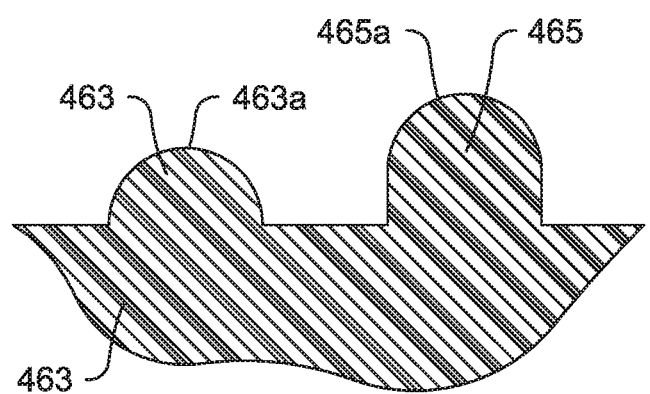
FIG. 26 is a highly magnified partial sectional view of the plunger of FIG. 23.
Figure 27:
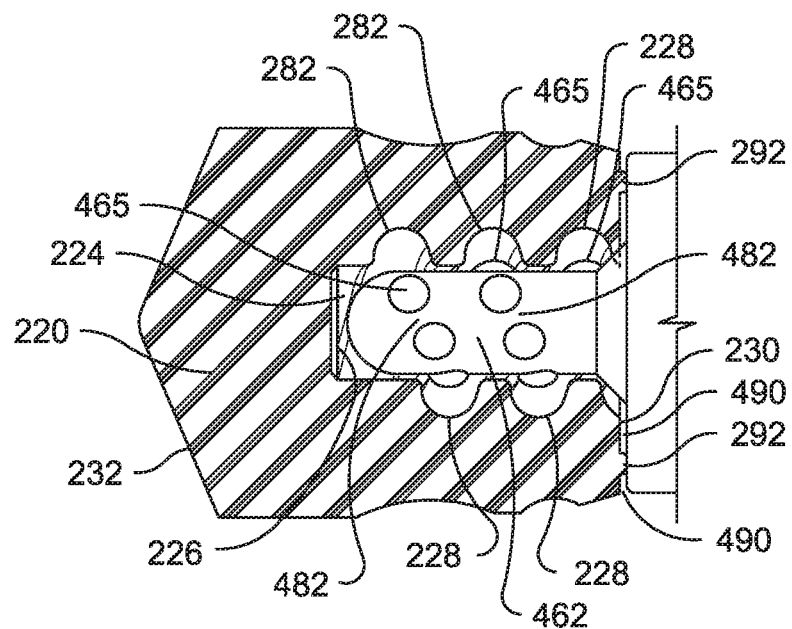
FIG. 27 is a magnified right side partial sectional view of the plunger assembly of FIG. 23.
Figure 28:
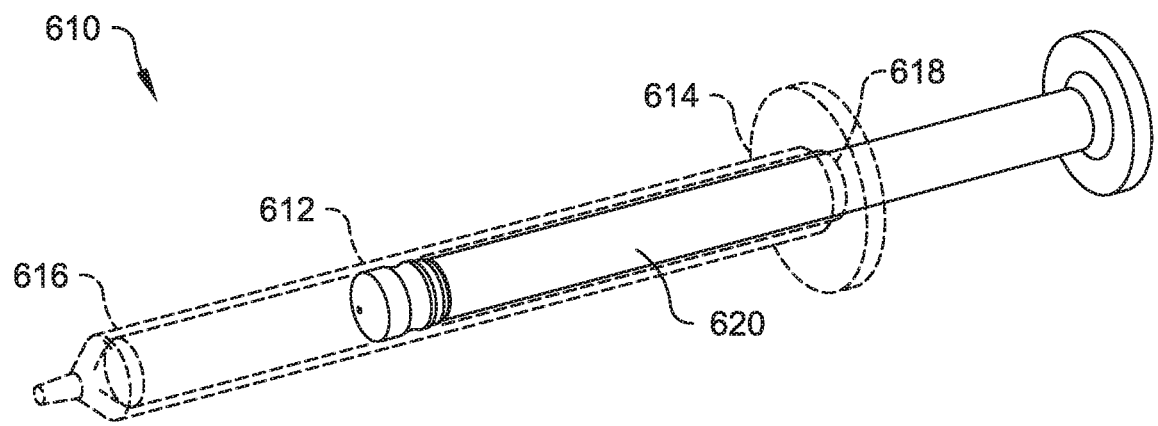
FIG. 28 is a front right perspective view of an embodiment of a fluid-dispensing syringe including a barrel and a plunger assembly.

Referring to FIG. 28, any of the plunger assemblies disclosed herein may be incorporated into a fluid-dispensing syringe 610 comprising the plunger assembly and a syringe barrel 612 having a proximal end 614 and a distal end 616, with the proximal end 614 having a proximal barrel opening 618. An example of such a fluid-dispensing syringe 610 is shown in FIG. 26. The plunger assembly 620 may be disposed within the barrel 612 and may extend through the proximal barrel opening 618. The plunger assembly may be any known plunger assembly and may take the form of any of the plunger assemblies disclosed herein.

A method of preparing a sterile plunger assembly may be practiced with a plunger assembly including a piston and a plunger, such as any of the plunger assemblies disclosed herein. The method may comprise: engaging a piston with a plunger rod to form a plunger assembly with a cavity, such as any of the plunger assemblies described above; and introducing a sterilizing fluid into the space outside the plunger assembly so that the sterilizing fluid may pass into the piston cavity for sterilization thereof.

A method of preparing a sterile fluid-dispensing syringe may be practiced with a plunger assembly, of which an example is shown in FIG. 28 as element 620, which may include any of the plunger assemblies disclosed herein. The method may comprise: engaging a piston with a plunger rod to form a plunger assembly 620, such as a plunger assembly as described herein; inserting the plunger assembly 620 into a syringe barrel such as the syringe barrel 612 shown in FIG. 28 having a proximal end 614 and a distal end 616, the proximal end 614 having a proximal barrel opening 618; introducing a sterilizing fluid into the space outside the plunger assembly 620 so that the sterilizing fluid passes into the piston cavity for sterilization thereof.

It will be appreciated by those skilled in the art that changes could be made to the embodiments described above without departing from the broad inventive concept thereof. For example, the materials of construction, dimensions, thread profiles, and other details of the disclosed embodiments may be readily modified to alternatives known to those skilled in the relevant art. It is understood, therefore, that this invention is not limited to the particular embodiments disclosed, but it is intended to cover modifications within the spirit and scope of the present invention as defined by the appended claims. Moreover, aspects and features of various embodiments may be combined in a particular device; and fewer that all of the aspects and features of a particular embodiment disclosed herein may be sufficient for a functional embodiment.

In addition, certain terminology is used in the following description for convenience only and is not limiting. The words "lower," "bottom," "upper," "top," "front," "back," and "rear" designate directions in the drawings to which reference is made. The words "inwardly" and "outwardly" refer to directions toward and away from, respectively, the geometric center of the component being discussed, and designated parts thereof, in accordance with the present disclosure. Unless specifically set forth herein, the terms "a," "an," and "the" are not limited to one element, but instead should be read as meaning "at least one." "At least one" may occasionally be used for clarity or readability, but such use does not change the interpretation of "a," "an," and "the." The terminology includes the words noted above, derivatives thereof, and words of similar import. Moreover, the singular includes the plural, and vice versa, unless the context clearly indicates otherwise. Various components are described in terms of a single component; however, the illustrated embodiment, or other embodiments not illustrated, may include two or more of the same component, as illustrated in the drawings or noted in the specification, or as otherwise would be understood by a person of skill in the art. Various components are described as being secured against movement or flexing; these references do not contemplate the absolute elimination of all movement or flexing. Instead, these references include restriction or movement of flexing sufficient to alter the functionality of the component or components in operative relation therewith. References to a component extending, moving, or flexing in a particular direction refer to the component extending, moving, or flexing at least partially in the particular direction; an extension, movement, or flexion that includes any component of movement in the particular direction is included.

We claim:

1. A plunger assembly comprising:
   a piston comprising an inner piston surface, a female thread, an outer surface that faces outwardly relative to a longitudinal axis of the piston, and a proximal-facing piston surface extending radially inwardly from the outer surface, wherein the inner piston surface and the female thread define an inner piston cavity; and
   a plunger rod comprising an outer surface that faces outwardly relative to a longitudinal axis of the plunger rod, a distal-facing rod surface extending radially inwardly from the outer surface of the plunger rod, and a threaded extension that extends a length distally from the distal-facing rod surface, wherein:
      the threaded extension is configured to threadedly engage with the female thread along at least a portion of the length,
      the threaded extension and the inner piston surface define a ventilation space when the plunger rod is fully advanced distally relative to the piston,
      the proximal-facing piston surface and the distal-facing rod surface, when the plunger rod is fully advanced distally relative to the piston, are spaced apart and define a fluid passageway therebetween,
      the fluid passageway extends from outside of the plunger assembly into the inner piston cavity,
      the fluid passageway comprises an inlet that fluidly connects the fluid passageway to outside of the plunger assembly, and
      the inlet of the fluid passageway is defined by a space between an edge of the proximal-facing piston surface that intersects with the outer surface of the piston and an edge of the distal-facing rod surface that intersects with the outer surface of the plunger rod.

2. The plunger assembly according to claim 1, wherein:
   the inner piston cavity comprises a proximal cavity end and a distal cavity end,
   the female thread is spaced apart from the distal cavity end,
   the threaded extension comprises a male thread,
   the male thread comprises a proximal male thread end and a distal male thread end,
   the male thread is configured such that, when the plunger rod is fully advanced distally, the proximal male thread end is located distally of the female thread, and
   the ventilation space is between the threaded extension and the inner piston surface.

3. The plunger assembly according to claim 1, wherein:
   the inner piston cavity comprises a proximal cavity end and a distal cavity end,
   the female thread is spaced apart from the distal cavity end,
   the threaded extension comprises:
      a thread shank comprising a proximal thread shank end and a distal thread shank end; and
      a male thread that extends from the thread shank, the male thread comprising a proximal male thread end and a distal male thread end, the proximal male thread end being spaced apart from the proximal thread shank end, and
   the ventilation space is between the threaded extension and the inner piston surface.

4. The plunger assembly according to claim 1, wherein: the outer surface of the plunger rod comprises an outer distal end surface and an outer side surface, and the plunger rod comprises an auxiliary passage that extends from at least one of the outer distal end surface or the outer side surface and that fluidly connects to the ventilation space.

5. The plunger assembly of claim 1, wherein:
   the proximal-facing piston surface is outside of the inner piston cavity,
   the inner piston cavity comprises an opening at an interface with the proximal-facing piston surface, and
   the interface is a proximal-terminal end of the inner piston cavity.

6. The plunger assembly according to claim 1, wherein:
   the inner piston cavity comprises a proximal cavity end and a distal cavity end,
   the female thread comprises a plurality of female threads, the plurality of female threads have a female-thread major diameter and a female-thread minor diameter;
   the threaded extension comprises:
      a thread shank comprising a proximal thread shank end and distal thread shank end, the thread shank having a variable diameter, and
      a plurality of male threads that extend from the thread shank, the plurality of male threads have a constant male thread major diameter; and
   the ventilation space is between the thread shank and the female-thread minor diameter.

7. The plunger assembly according to claim 6, wherein the ventilation space comprises a plurality of spaces between the thread shank and the female-thread minor diameter.

8. The plunger assembly according to claim 7, wherein: the outer surface of the plunger rod comprises an outer distal end surface and an outer side surface, and the plunger rod comprises an auxiliary passage that extends from at least one of the outer distal end surface or the outer side surface and that fluidly connects to the ventilation space.

9. The plunger assembly according to claim 1, wherein:
the threaded extension comprises a thread shank and a discontinuous male thread comprising a plurality of protrusions that extend from the thread shank; and
the ventilation space is between the plurality of protrusions.

10. The plunger assembly according to claim 9, wherein the plurality of protrusions comprises at least one of a hemispherical body or a rod-shaped body with a hemispherical radially outward portion.

11. The plunger assembly according to claim 9, wherein the thread shank has a variable male thread shank diameter.

12. The plunger assembly of claim 9, wherein: the outer surface of the plunger rod comprises an outer distal end surface and an outer side surface, and the plunger rod comprises an auxiliary passage that extends from at least one of the outer distal end surface or the outer side surface and that fluidly connects to the ventilation space.

13. The plunger assembly according to claim 1, wherein:
the inner piston cavity comprises a proximal cavity end and a distal cavity end;
the female thread comprises a plurality of female threads, the plurality of female threads having a female-thread major diameter and a female-thread minor diameter;
the threaded extension comprises:
a thread shank with a thread shank axis; and
a plurality of male threads that extend from the thread shank, the plurality of male threads having a truncated portion; and
the ventilation space is between the truncated portion and the plurality of female threads.

14. The plunger assembly according to claim 13, wherein:
the truncated portion comprises a planar cut portion of the plurality of male threads; and
the ventilation space is between the planar cut portion and the plurality of female threads.

15. The plunger assembly according to claim 13, wherein: the outer surface of the plunger rod comprises an outer distal end surface and an outer side surface, and the plunger rod comprises an auxiliary passage that extends from the outer side surface to the truncated portion.

16. The plunger assembly according to claim 13, wherein: the outer surface of the plunger rod comprises an outer distal end surface and an outer side surface, and the plunger rod comprises an auxiliary passage that extends from at least one of the outer distal end surface or the outer side surface to the truncated portion to connect to the ventilation space.

17. The plunger assembly according to claim 16, wherein the auxiliary passage extends from the outer side surface to the truncated portion.

18. A fluid-dispensing syringe comprising:
a syringe barrel; and
the plunger assembly of claim 1, wherein the piston is within the syringe barrel.

19. A method of sterilizing the plunger assembly of claim 1, the method comprising introducing a sterilizing fluid into an external environment surrounding the plunger assembly, thereby causing the sterilizing fluid to flow into the inner piston cavity and sterilize the inner piston cavity.

20. A method of sterilizing a fluid-dispensing syringe comprising the plunger assembly of claim 1 and a syringe barrel with the piston within the syringe barrel, the method comprising introducing a sterilizing fluid into the syringe barrel, thereby causing the sterilizing fluid to flow into the inner piston cavity and sterilize the inner piston cavity.

* * * * *